US010054297B1

United States Patent
Saeed

(10) Patent No.: US 10,054,297 B1
(45) Date of Patent: Aug. 21, 2018

(54) SALT LAMP ASSEMBLY

(71) Applicant: TIGER DIVE, LLC, Houston, TX (US)

(72) Inventor: Mansoor Saeed, Houston, TX (US)

(\*) Notice: Subject to any disclaimer, the term of this patent is extended or adjusted under 35 U.S.C. 154(b) by 0 days.

(21) Appl. No.: 15/642,602

(22) Filed: Jul. 6, 2017

(51) Int. Cl.
| F21V 19/04 | (2006.01) |
| F21S 6/00 | (2006.01) |
| F21V 17/06 | (2006.01) |
| F21W 121/00 | (2006.01) |

(52) U.S. Cl.
CPC ............ F21V 19/04 (2013.01); F21S 6/002 (2013.01); F21V 17/06 (2013.01); F21W 2121/00 (2013.01)

(58) Field of Classification Search
CPC .......... F21S 6/002; F21S 10/005; F21V 3/61; F21V 3/04; F21V 3/02; F21V 3/0061; F21V 3/0062; F21V 5/00; F21W 2121/00; G02B 27/0944
See application file for complete search history.

(56) References Cited

U.S. PATENT DOCUMENTS

| 3,793,755 | A | * | 2/1974 | Gersch | F21S 10/02 40/433 |
| 6,078,426 | A | * | 6/2000 | Siegfried | F21V 9/12 359/591 |
| 6,362,572 | B1 | * | 3/2002 | Hepburn | H01J 61/16 313/485 |
| 7,401,935 | B2 | * | 7/2008 | Vanderschuit | F21V 33/0028 362/101 |
| 2005/0180146 | A1 | * | 8/2005 | Vanderschuit | F21S 10/06 362/367 |

FOREIGN PATENT DOCUMENTS

| CN | 2637895 Y | * | 9/2004 |
| CN | 201568881 U | * | 9/2010 |
| CN | 201666533 U | * | 12/2010 |

\* cited by examiner

*Primary Examiner* — Hargobind S. Sawhney
(74) *Attorney, Agent, or Firm* — Matthew M. Googe; Robinson IP Law, PLLC

(57) ABSTRACT

A salt lamp assembly includes: a crystal body having a hollow cavity formed within the crystal body and a base attached to a bottom end of the crystal body; a retaining plate attached to the base the crystal body, the retaining plate including an aperture formed through a center of the retaining plate and at least one passage formed adjacent the aperture; and a light source plate removably inserted into the hollow crystal body through the aperture of the retaining plate, the light source plate including a socket and at least one clip extending upwardly from the light source plate for engaging the retaining plate through the at least one passage.

6 Claims, 9 Drawing Sheets

SALT LAMP ASSEMBLY

FIELD

This disclosure relates to the field of lamps. More particularly, this disclosure relates to a salt lamp assembly.

BACKGROUND

Salt lamps, also called Himalayan salt lamps, provide a decorative light element and typically include a large salt crystal. The salt crystal is typically illuminated by a light source, such as a light bulb. The salt crystal is illuminated by the light source to produce a soothing glow. The illuminated salt crystal may also impart additional health benefits.

The light source is typically fixed within the salt crystal such that removal and replacement of the light source is difficult. For example, the light source may be secured within the salt crystal with fasteners or an adhesive. However, subsequent removal of the light source may be difficult and require tools or breaking of an adhesive bond. This makes both replacement of the light source or swapping of the salt crystal difficult.

What is needed, therefore, is a salt lamp assembly that enables the light source to be readily installed and removed from a salt crystal.

SUMMARY

The above and other needs are met by a salt lamp assembly that enables the light source to be readily installed and removed from a salt crystal. In a first aspect a salt lamp assembly includes: a crystal body having a hollow cavity formed within the crystal body and a base attached to a bottom end of the crystal body; a retaining plate attached to the base the crystal body, the retaining plate including an aperture formed through a center of the retaining plate and at least one passage formed adjacent the aperture; and a light source plate removably inserted into the hollow crystal body through the aperture of the retaining plate, the light source plate including a socket and at least one clip extending upwardly from the light source plate for engaging the retaining plate through the at least one passage.

In one embodiment, the base of the crystal body further includes a recessed center portion, the retaining plate and light source plate fitting within the recessed center portion when the light source plate is engaged with the retaining plate.

In another embodiment, the base of the crystal body further includes one more indentations formed through an edge of the base of the crystal body.

In yet another embodiment, the retaining plate further includes an upwardly projecting ring formed around the aperture of the retaining plate.

In one embodiment, the retaining plate further includes an edge formed between the upward projecting ring and the aperture of the retaining plate, wherein the at least one clip of the light source plate engages the edge when the light source plate is rotated with respect to the retaining plate.

In a second aspect, a salt lamp assembly includes: a crystal body having a hollow cavity formed within the crystal body and a base attached to a bottom end of the crystal body, the base of the crystal body further comprising a recessed center portion; a retaining plate attached to the base the crystal body, the retaining plate including an aperture formed through a center of the retaining plate, at least one passage formed adjacent the aperture, an upwardly projecting ring formed around the aperture of the retaining plate, and an edge formed between the upward projecting ring and the aperture of the retaining plate, wherein the at least one clip of the light source plate engages the edge when the light source plate is rotated with respect to the retaining plate; and a light source plate removably inserted into the hollow crystal body through the aperture of the retaining plate, the light source plate including a socket and at least one clip extending upwardly from the light source plate for engaging the retaining plate through the at least one passage.

BRIEF DESCRIPTION OF THE DRAWINGS

Further features, aspects, and advantages of the present disclosure will become better understood by reference to the following detailed description, appended claims, and accompanying figures, wherein elements are not to scale to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Figure 1:
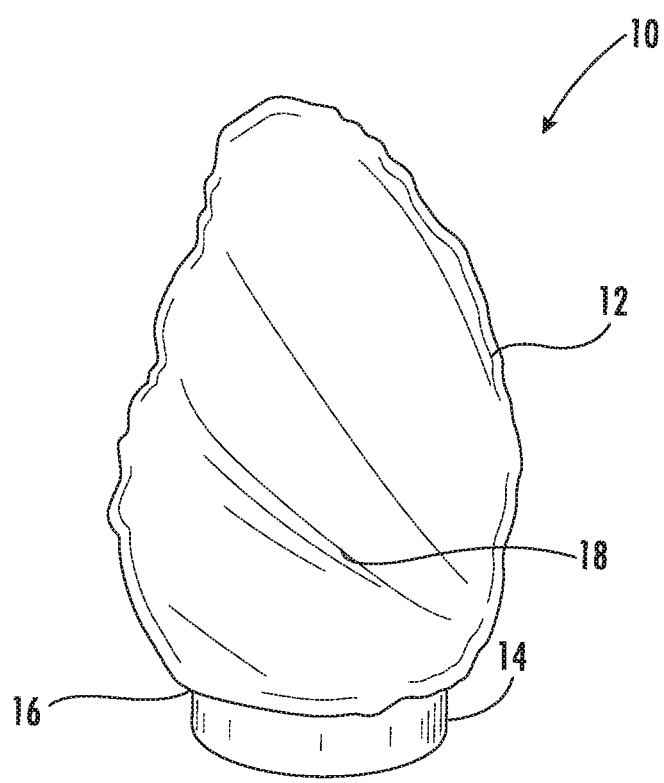
FIG. 1 shows a salt lamp according to one embodiment of the present disclosure.

FIG. 1 shows a basic embodiment of a salt lamp 10 according to embodiments of the present disclosure. The salt lamp 10 includes a hollow crystal body 12 attached to a base 14, the base preferably made of wood. The base 14 is preferably fixed to the crystal body 12 at a bottom end 16 of the crystal body 12, such as with an adhesive or fasteners inserted through the base into the crystal body 12. A light source 18 is mounted on the base and extends into the hollow crystal body 12 such that the light source 18 illuminates the hollow crystal body 12. The light source 18 is mounted to the base 14 such that the light source 18 is easily removable from within the crystal body 12.

Figure 2:
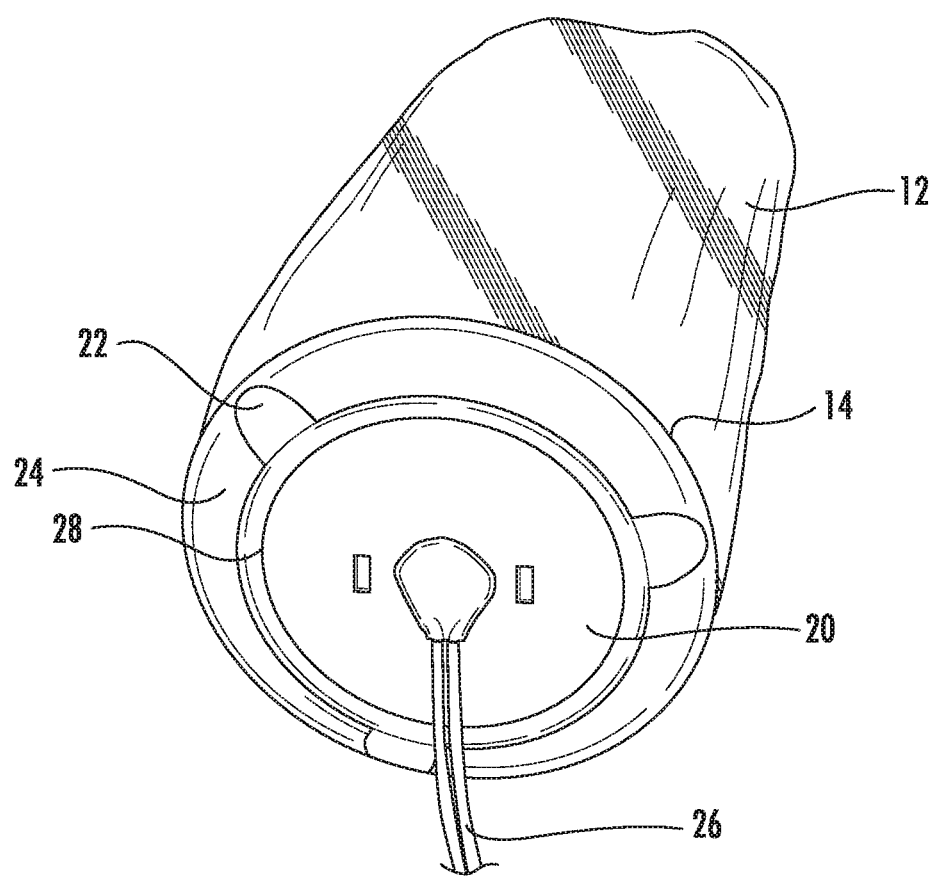
FIG. 2 shows a perspective bottom view of a salt lamp according to one embodiment of the present disclosure.

Referring now to FIG. 2, the base 14 includes a light source plate 20 attached to the base 14. The light source plate 20 is removably attached to the base 14 as discussed in greater detail below. The base 14 includes one or more indentations 22 formed around an edge 24 of the base 14. The one or more indentations 22 are shaped such that a cord 26 for supplying power to the light source 18 may fit within the one or more indentations 22. When the salt lamp 10 is resting on a flat surface, such as a table, the cord 26 is positioned through the one or more indentations 22 such that the base 14 of the salt lamp 10 sits flush with the flat surface.

A central portion 28 of the base 14 is preferably recessed such that the light source plate 20 fits within the recessed central portion 28. The light source plate 20 is preferably circular in shape and is concentrically aligned within the recessed central portion 28 of the base 14.

Figure 3:
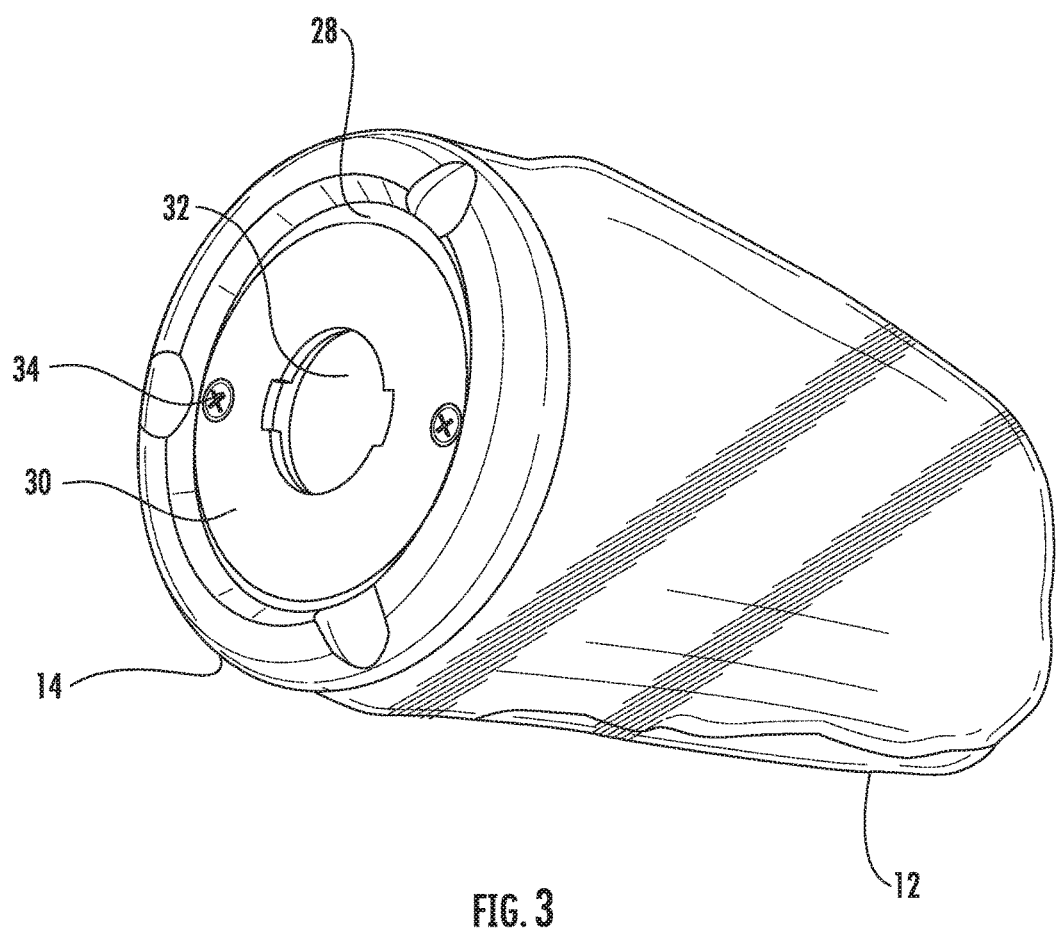
FIG. 3 shows a perspective bottom view of a salt lamp with the light source plate removed according to one embodiment of the present disclosure.

FIG. 3 shows a bottom view of the salt lamp 10 with the light source plate 20 removed. A retaining plate 30 is associated with the base 14 within the recessed portion 28 of the base 14. The retaining plate 30 is also preferably circular in shape and is concentrically aligned within the recessed portion 28 of the base 14. The retaining plate 30 includes an aperture 32 formed through a center of the retaining plate 30. The aperture 32 is sized to receive the light source 18 (FIG. 11) through the aperture when the light source plate 20 (FIG. 2) is engaged with the retaining plate 30, as discussed in greater detail below. The retaining plate 30 is preferably fixed to the base 14, such as with one or more fasteners 34 inserted through the retaining plate 30 and into the base 14. In one embodiment, the base 14 and retaining plate 30 are formed as a single component, such as by molding the base 14 and retaining plate 30 as a single piece that is attached to the hollow crystal body 12.

Figure 4A:
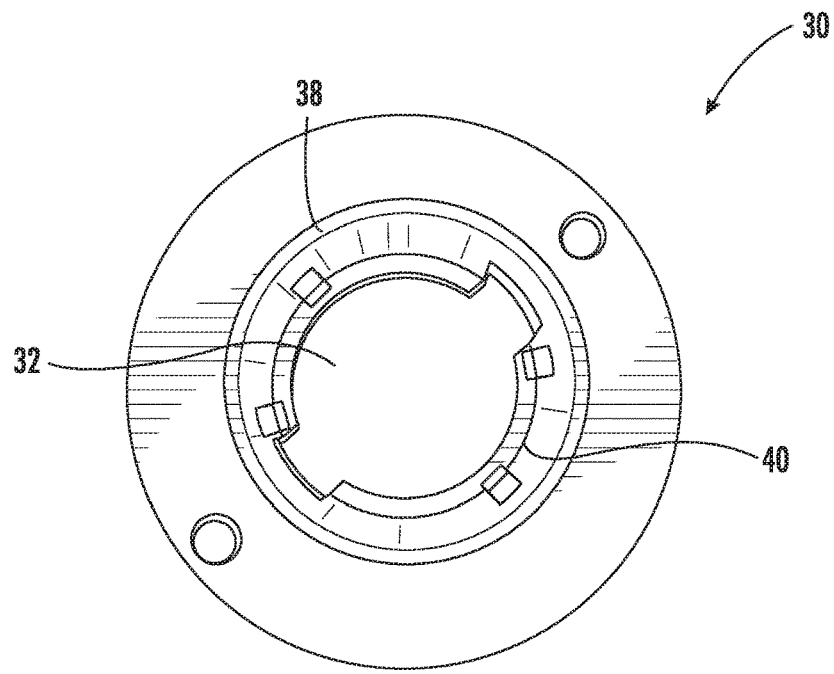
FIGS. 4A and 4B show a retaining plate according to one embodiment of the present disclosure.
Figure 4B:
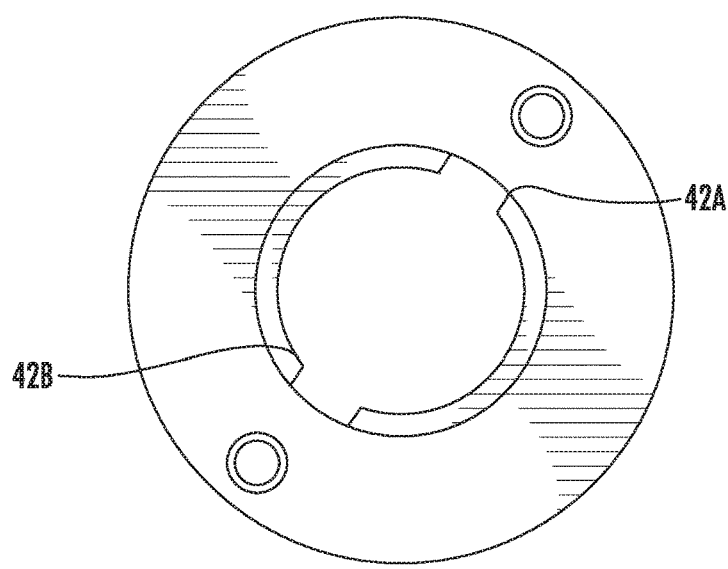

FIG. 4A shows a top view of the retaining plate 30. The retaining plate 30 includes a flange 36 formed around the aperture 32. A ring 38 projects upwardly from the flange 36 around the aperture 32. The ring 38 extends into the base 14 when the ring 38 is fastened to the base 14. An edge 40 is formed within the ring 38 and around the aperture 32. Referring to FIG. 4B, the flange 36 includes one or more fastener apertures 41 formed through the flange 36 for receiving one or more fasteners for attaching the retaining plate 30 to the base.

Figure 5:
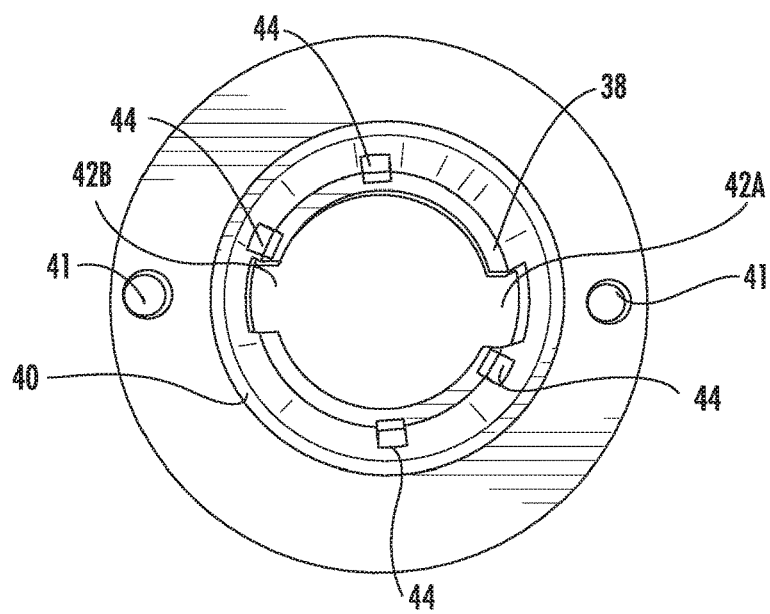
FIGS. 5 and 6 illustrate a retaining plate according to one embodiment of the present disclosure.
Figure 6:
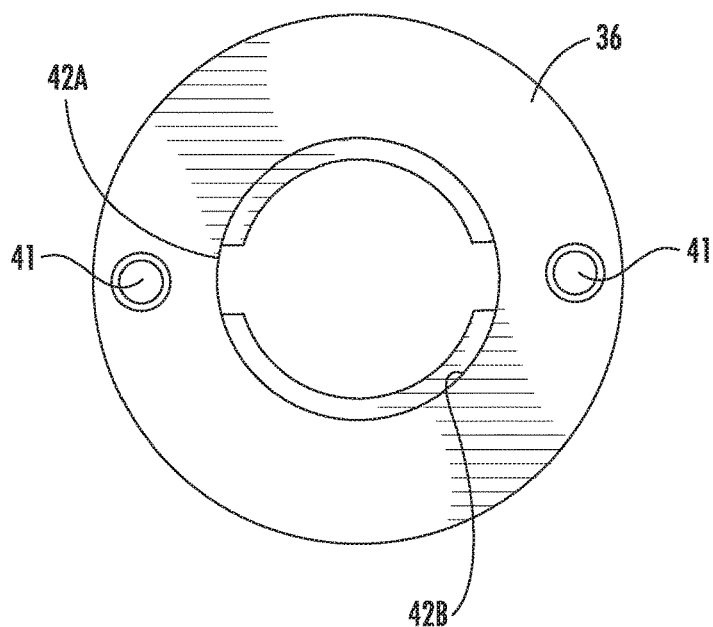

A pair of opposing passages 42A and 42B are formed through the edge 40. Referring to FIGS. 5 and 6, the opposing passages 42A and 42B are formed through the edge 40 adjacent to the aperture 32. A plurality of tabs 44 are formed along an inner edge of the ring 38 around the edge 40 for contacting a portion of the light source plate 20, as described below.

Figure 7:
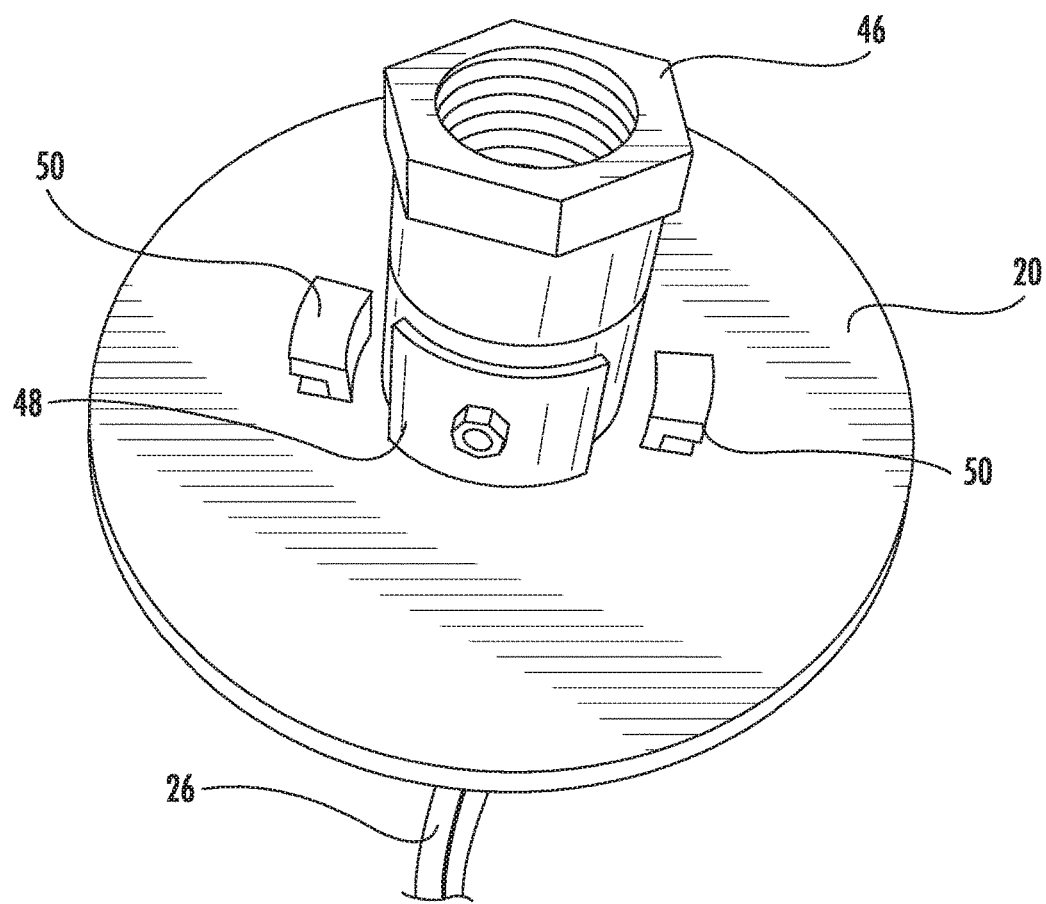
FIG. 7 shows a light source plate according to one embodiment of the present disclosure.

The light source plate 20 includes light source holder 46 attached to the light source plate 20 through a center of the light source plate 20. The light source holder 46 is attached to the light source plate 20 through one or more tabs 48 projecting upwardly from the light source plate 20. The light source holder 46 is preferably attached to the one or more tabs 48 with one or more fasteners. The light source holder 46 includes socket 49 for threadably engaging a light source, such as a light bulb. While the above and FIG. 7 illustrate the light source holder 46 attached to the light source plate 20 as two separate components, in one embodiment the light source holder 46 and light source plate 20 are formed of a single piece, such as a single molded piece.

Figure 8:
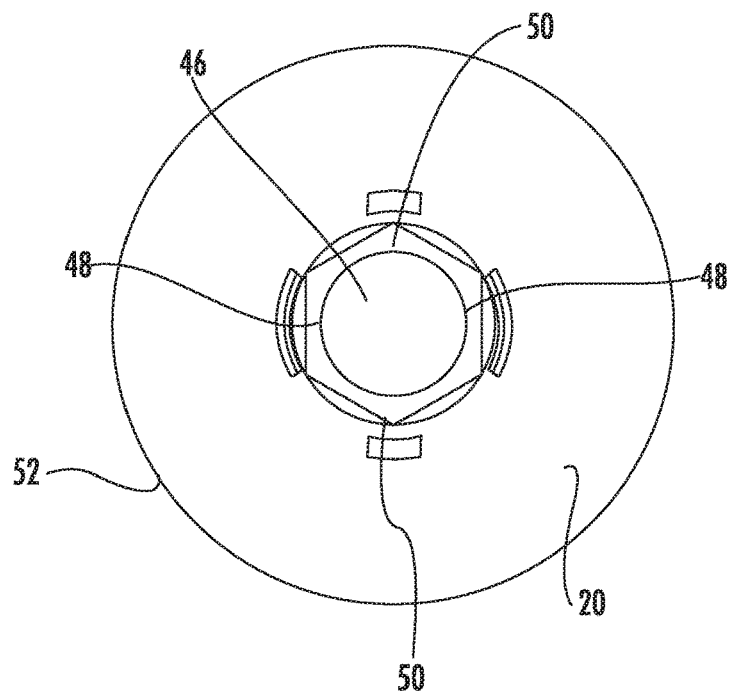
FIGS. 8 and 9 illustrate a light source plate according to one embodiment of the present disclosure.
Figure 9:
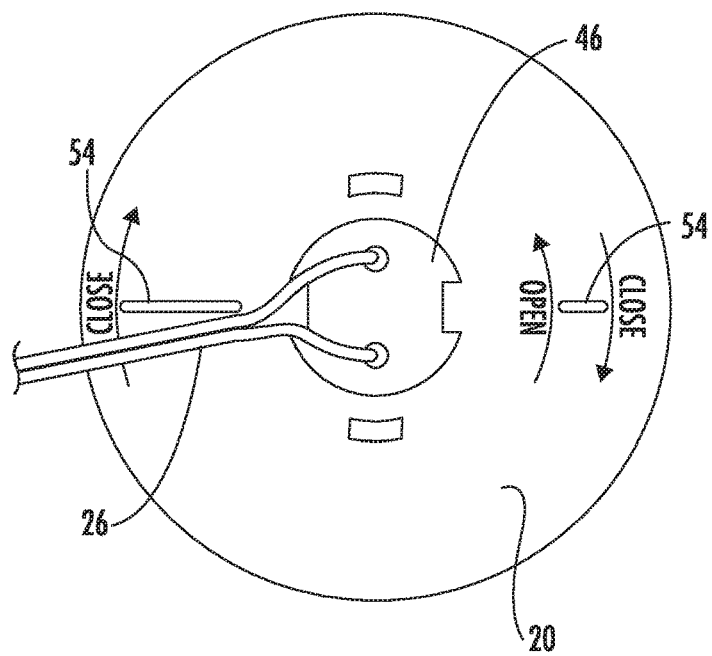
Figure 10:
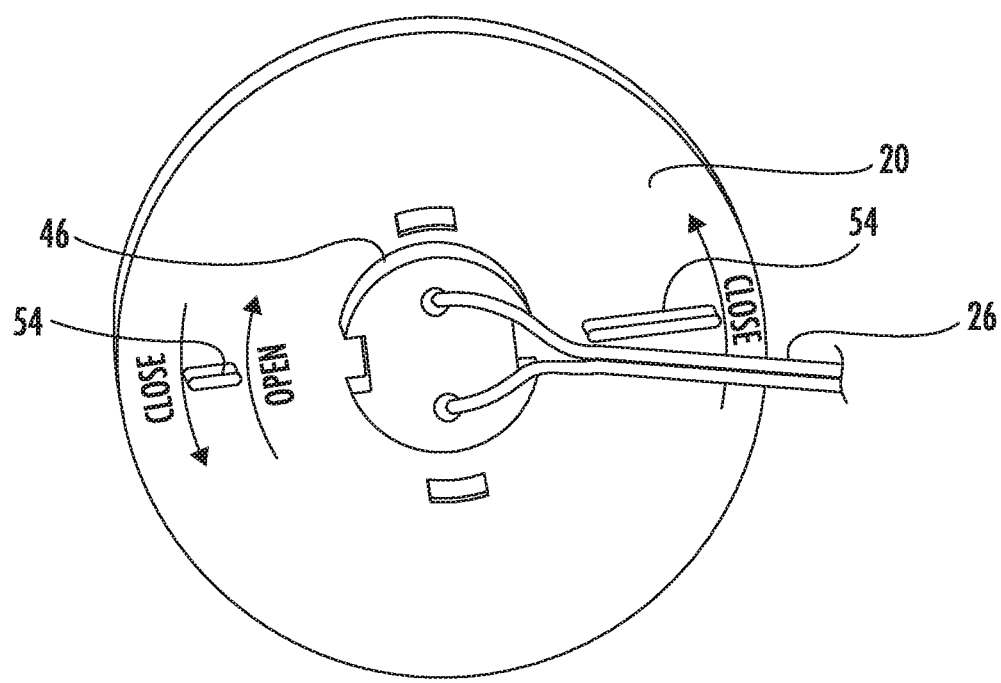
FIG. 10 shows a bottom view of a light source plate according to one embodiment of the present disclosure.

Referring to FIG. 8, the light source plate 20 also includes a pair of opposing clips 50 extending upwardly from the light source plate 20. The opposing clips 50 are outwardly facing such that an open end of each clip 50 faces an outer edge 52 of the light source plate 20. As shown in FIGS. 9 and 10, one or more opposing finger tabs 54 are formed on a bottom of the light source plate 20 such that a user may engage and rotate the light source plate 20 as described herein.

Figure 11:
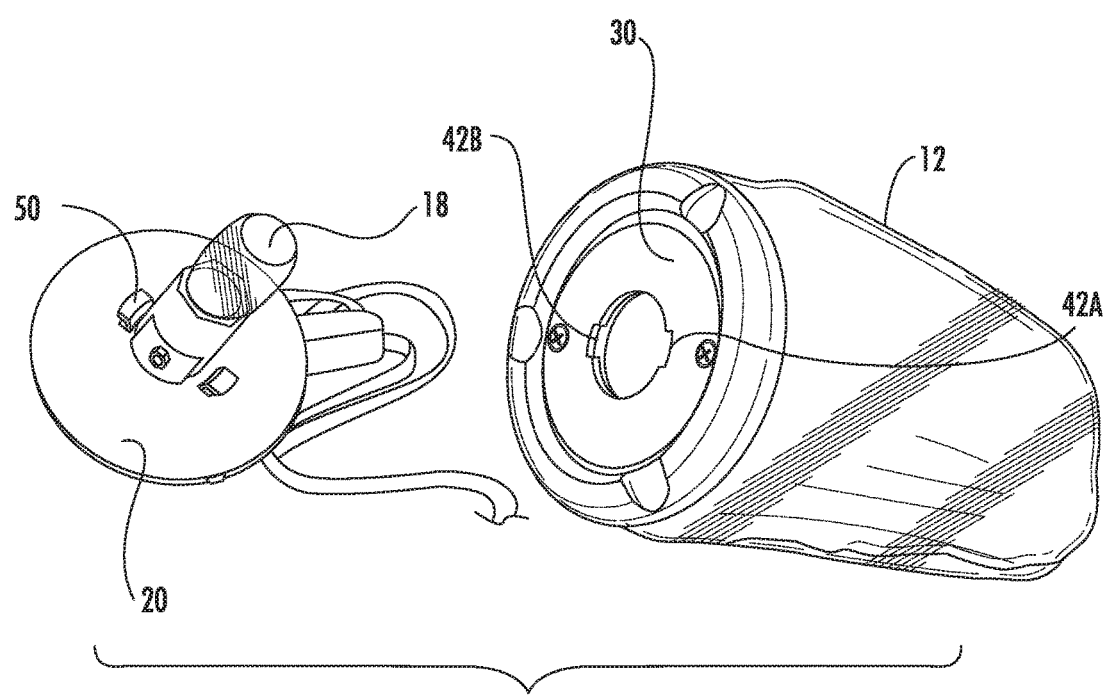
FIG. 11 shows a salt lamp with the light source removed according to one embodiment of the present disclosure.

Referring now to FIG. 11, the light source plate 20 is engaged with the retaining plate 30 by first inserting the light source 18 through the aperture 32 of the retaining plate 30. The one or more clips 50 are aligned with the opposing passages 42A and 42B such that the one or more clips 50 pass through the opposing passages 42A and 42B and the light source 18 is inserted into the crystal body 12. After the one or more clips 50 are inserted into opposing passages 42A and 42B, the light source plate 20 is rotated with respect to the retaining plate 30. When the light source plate 20 is rotated, the one or more clips 50 engage the edge 40 of the retaining plate 30 such that the one or more clips 50 secure the light source plate 20 to the retaining plate 30 along the edge 40 of the retaining plate 30. The light source plate 20 is rotated until the one or more clips 50 contact one of the plurality of tabs 44 of the retaining plate 30, thereby preventing further rotation of the light source plate 20. To remove the light source plate 20 and attached light source 18, the light source plate 20 is rotated in an opposite direction until the one or more clips are aligned with the opposing passages 42A and 42B, thereby disengaging the one or more clips 50 from the edge 40 of the retaining plate 30.

The salt lamp 10 of the present disclosure advantageously allows a user to insert and remove the light source 18 from the crystal body 12. Allowing the user to readily insert and remove the light source 18 allows a user to easily change the light source 18 in the event that the light source expires 18. Further, the user may swap the light source 18 to change a color of illumination of the crystal body 12, or may swap the crystal body 12 without requiring any tools.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A salt lamp assembly comprising:
   a crystal body having a hollow cavity formed within the crystal body and a base attached to a bottom end of the crystal body;
   a retaining plate associated with the base of the crystal body, the retaining plate including an aperture formed through a center of the retaining plate and at least one passage formed adjacent the aperture; and
   a light source plate removably inserted into the hollow crystal body through the aperture of the retaining plate, the light source plate including a socket and at least one clip extending upwardly from the light source plate for engaging the retaining plate through the at least one passage.

2. The salt lamp assembly of claim 1, the base of the crystal body further comprising a recessed center portion, the retaining plate and light source plate fitting within the recessed center portion when the light source plate is engaged with the retaining plate.

3. The salt lamp assembly of claim 1, the base of the crystal body further comprising one more indentations formed through an edge of the base of the crystal body.

4. The salt lamp assembly of claim 1, the retaining plate further comprising an upwardly projecting ring formed around the aperture of the retaining plate.

5. The salt lamp assembly of claim 4, the retaining plate further comprising an edge formed between the upward projecting ring and the aperture of the retaining plate, wherein the at least one clip of the light source plate engages the edge when the light source plate is rotated with respect to the retaining plate.

6. A salt lamp assembly comprising:
- a crystal body having a hollow cavity formed within the crystal body and a base attached to a bottom end of the crystal body, the base of the crystal body further comprising a recessed center portion;
- a retaining plate attached to the base the crystal body, the retaining plate including an aperture formed through a center of the retaining plate, at least one passage formed adjacent the aperture, an upwardly projecting ring formed around the aperture of the retaining plate, and an edge formed between the upward projecting ring and the aperture of the retaining plate, wherein the at least one clip of the light source plate engages the edge when the light source plate is rotated with respect to the retaining plate; and
- a light source plate removably inserted into the hollow crystal body through the aperture of the retaining plate, the light source plate including a socket and at least one clip extending upwardly from the light source plate for engaging the retaining plate through the at least one passage.

\* \* \* \* \*